United States Patent [19]

Fine et al.

[11] Patent Number: 5,175,089
[45] Date of Patent: Dec. 29, 1992

[54] METHOD FOR MONITORING PERIODONTAL DISEASE BY MONITORING ENDOTOXINS AND INFLAMMATORY AGENTS

[75] Inventors: Daniel H. Fine, Leonia, N.J.; Spyros Vratsanos, Syosset, N.Y.

[73] Assignee: The Trustees of Columbia University, in the City of New York, New York,

[21] Appl. No.: 219,584

[22] Filed: Jul. 15, 1988

[51] Int. Cl.⁵ .......................... C12Q 1/37; C12Q 1/04; C12Q 1/06; G01N 33/579
[52] U.S. Cl. ........................................ 435/23; 435/30; 435/34; 435/39; 435/183; 435/810; 435/805; 435/184; 435/184 M; 436/903
[58] Field of Search .................. 435/23, 184, 213, 810, 435/30, 34, 183; 530/802, 300, 330, 331; 436/903

[56] References Cited

U.S. PATENT DOCUMENTS 4,188,264 2/1980 Iwanaga et al. ...................... 435/19
4,301,245 11/1981 Lindsay et al. ...................... 435/23
4,510,241 5/1985 Mills ..................................... 435/23

FOREIGN PATENT DOCUMENTS 0151536 8/1985 European Pat. Off. ............. 435/16

OTHER PUBLICATIONS

McCoy, S. A., et al.; Biological Abstracts, vol. 84, No. 6, abstract #57227 (1987).
Moore, J. M., et al., Biological Abstracts, vol. 83, No. 3, abstract #25026 (1987).
Fine, D. H., et al., Biological Abstracts, vol. 69, No. 10, abstract #65455 (1980).
Norwitz et al., "Spectophotometric Determination of Aniline by the Diazotization-Coupling Method with N-Cl-Naphthyldethylenediamine as the Coupling Agent", Anal. Chem. (1981), vol. 53 (8), pp. 1238-1240.
Kurimoto, T. et al., Infect. Immun., vol. 51, No. 3, pp. 969-971 (1986).
Fine, D. H., et al, Biological Abstracts, vol. 66, abstract No. 15384 (1978).
Tufano, M. A. et al., Index Medicus, Medline abstract No. 87038839 (Oct. 1986).
Zambon, J. J., Index Medicus, Medline abstract No. 85131868 (Jan. 1985).
Slots, J., et al., Index Medicus, Medline abstract No. 85262066.

Primary Examiner—Esther L. Kepplinger
Assistant Examiner—Toni R. Scheiner
Attorney, Agent, or Firm—John P. White; Craig J. Arnold

[57] ABSTRACT

The present invention concerns a method of quantitatively determining the amount of bacterial endotoxin present in a periodontal pocket of a subject. The method comprises:
a) obtaining a sample from the periodontal pocket of the subject;
b) contacting the sample with an amebocyte lysate under conditions so as to activate an enzyme capable of cleaving a bond between an arginyl group and a nitrogen-containing group;
c) contacting the activated enzyme with a substrate comprising an arginyl group and a suitable nitrogen-containing group bound to the arginyl group so as to form an amine;
d) treating the resulting amine to produce a detectable product; and
e) quantitatively determining the amount of product formed and thereby the amount of bacterial endotoxins present in the periodontal pocket.

The invention also provides a method of diagnosing a periodontal disease which comprises quantitatively determining the amount of bacterial endotoxins present in a periodontal pocket of a subject by the method of the present invention and correlating the amount so determined with known periodontal disease-causing amounts of endotoxin.

15 Claims, 5 Drawing Sheets

METHOD FOR MONITORING PERIODONTAL DISEASE BY MONITORING ENDOTOXINS AND INFLAMMATORY AGENTS

BACKGROUND OF THE INVENTION

Bacterial endotoxins are produced by Gram negative bacteria, many of which are very dangerous or deadly in human beings and animals. In periodontal pockets, Gram-negative bacteria, their endotoxins and other inflammatory agents cause gingivitis and other periodontal diseases It is important to identify the existence of endotoxins and, if possible, the concentration of the endotoxins in the periodontal pockets in order to promptly initiate the proper medical and dental treatment. The monitoring of endotoxins in the periodontal pockets of a subject may also be used to diagnose periodontal diseases and the effect of treatment programs.

It has been known for many years that bacterial endotoxins activate the blood clotting enzyme occurring in amebocyte lysates of horseshoe crabs. This property has been described in many publications, e.g. J. Levin and F. B. Bangs, 1968, Thomb. Diath. Haemonth. 19:186 and S. Nakamura, 1976, Biochemical and Biophysical Research Communication, 72:902. These investigations demonstrated that the coagulation of Limulus amebocyte lysate (LAL) requires activation of the proclotting enzyme by endotoxin in the presence of divalent cations. The active enzyme thus formed cleaves coagulogen at the C-carboxyl terminal between the glycine and arginine subunits. The cleaved coaculogen molecules polymerize and thus bring about coagulation. The first endotoxin tests were based on observation of the gel thus formed. The gelation reaction test method is deficient for use in monitoring periodontal disease because of the considerable length of time necessary to carry it out, because it does not accurately measure endotoxin concentration, because it is difficult to standardize and because it requires highly skilled experienced personnel to perform it.

Fluorogenic or chromogenic substrates have been used for the assay of many enzymes, e.g. trypsin, thrombin, thromboplastin, serine protease, plasmin and plasminogen. It was also realized that fluorogens or chromogens can be used as LAL-substrates. See e.g. Iwanaga, et al., 1978; Homeostatis, 7:183 and patent publications U.S. Pat. No. 4,188,265, U.S. Pat. No. 4,406,832 and U.S. Pat. No. 4,510,241. The use of chromogenic substrates nas become a means to both study and clinically monitor various enzymes and inhibitors in the complex coagulation processes of man. An extensive list of enzyme specific substrates are commercially available for measuring enzymes such as trypsin, thrombin, thromboplastin, plasmin, plasmin kallikrein, urokinase, and plasminogen. Iwanaga, et al., Hemostasis 7:183-188 (1978) discloses that synthetic substrates can be used to measure the level of endotoxin activated pro-clot enzyme in LAL prepared from the blood of both the Japanese (Tachypleus tridentatus) and the American (Limulus polyphemus) horseshoe crabs.

Chromogenic substrate methods for assaying bacterial endotoxins using Limulus amebocyte lysate are also described in pages 209-220 of "Biomedical Applications of the Horseshoe Crab" (1979) Allen R. Liss, Inc. and U.S. Pat. No. 4,301,245. However, these disclosures are directed to the testing of blood which may contain endotoxins or the testing of food for endotoxin contamination.

There are three methods commonly used for monitoring bacteria in a periodontal pocket:
1. Dark field or phase microscopy;
2. Cultural microbiological evaluation; and
3. Fluorescent antibody identification.

The first method is inaccurate, time consuming, and requires the knowledge of a specialist. The second method is expensive and too cumbersome to be undertaken by the dentist in his office. The third method is also difficult for the dentist, and too expensive to be performed at each individual periodontal pocket site.

With the present method, it is possible to conduct the desired endotoxin test within a short period of time in a dental office and without the need for a specialist or expensive equipment. The time period for the method of the present invention is much shorter than that required for previous test methods for bacterial endotoxins. Moreover, the present method simply and accurately measures the concentration of the endotoxin to indicate the extent of the Gram negative bacterial infection in the periodontal pocket.

SUMMARY OF THE INVENTION

The present invention concerns a method of quantitatively determining the amount of bacterial endotoxin present in a periodontal pocket of a subject. The method comprises:

a) obtaining a sample from the periodontal pocket of the subject;

b) contacting the sample with an amebocyte lysate under conditions so as to activate an enzyme capable of cleaving a bond between an arginyl group and a nitrogen-containing group;

c) contacting the activated enzyme with a substrate comprising an arginyl group and a suitable nitrogen-containing group bound to the arginyl group so as to form an amine;

d) treating the resulting amine to produce a detectable product; and e) quantitatively determining the amount of product formed and thereby the amount of bacterial endotoxins present in the periodontal pocket.

In the preferred embodiments, the method comprises treating the sample prior to contacting with the amebocyte lysate so as to inactivate enzymes present in the sample which would interfere with amebocyte lysate-endotoxin interaction.

The invention also provides a method of diagnosing a periodontal disease which comprises quantitatively determining the amount of bacterial endotoxins present in a periodontal pocket of a subject by the method of the present invention and correlating the amount so determined with known periodontal disease-causing amounts of endotoxin. The invention also provides kits for carrying art the methods.

DETAILED DESCRIPTION OF THE INVENTION

Figure 1:
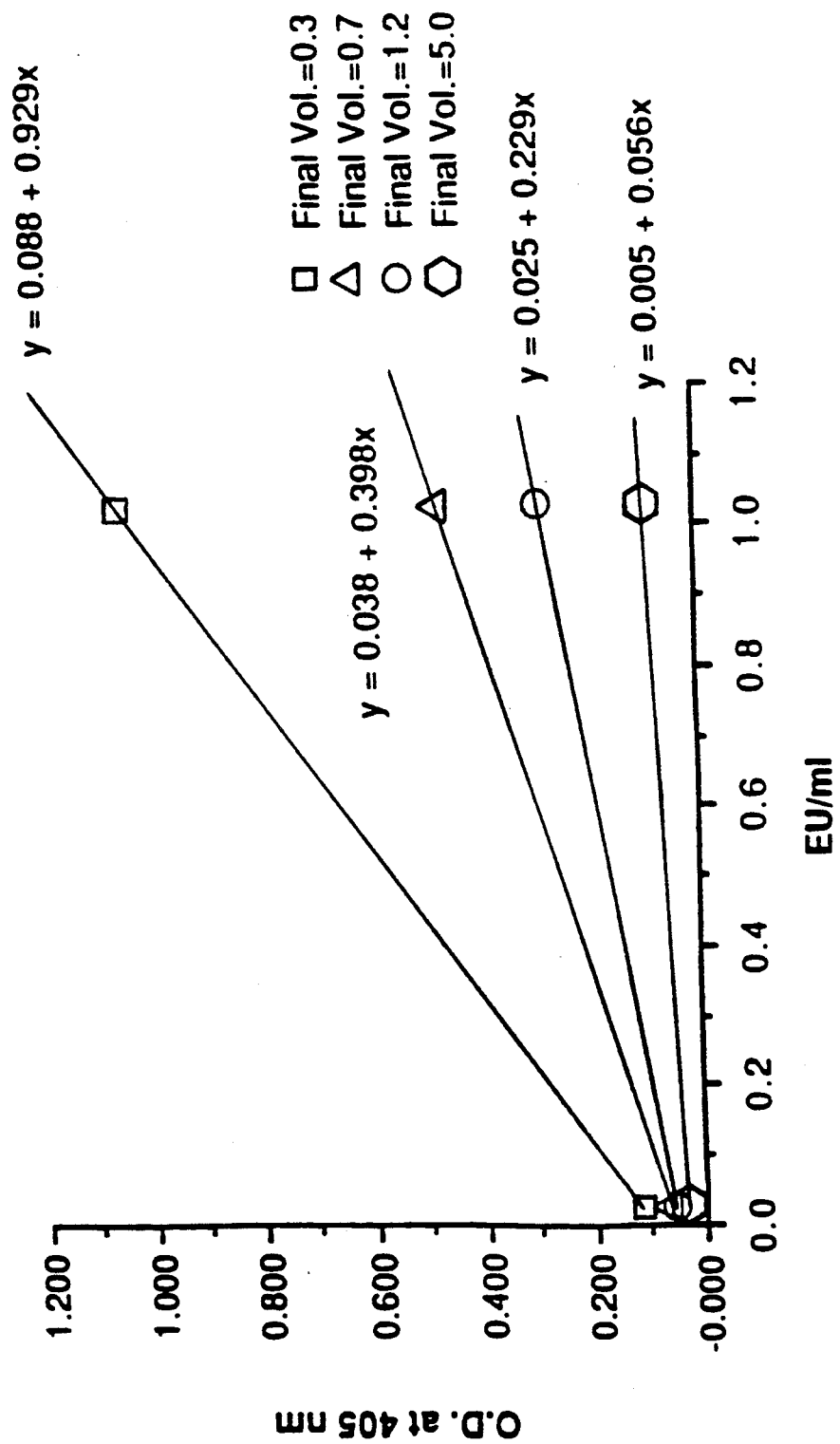
FIG. 1 shows the optical densities of the final volumes of p-nitroaniline measured at various endotoxin concentrations of the reaction mixture.
Figure 2:
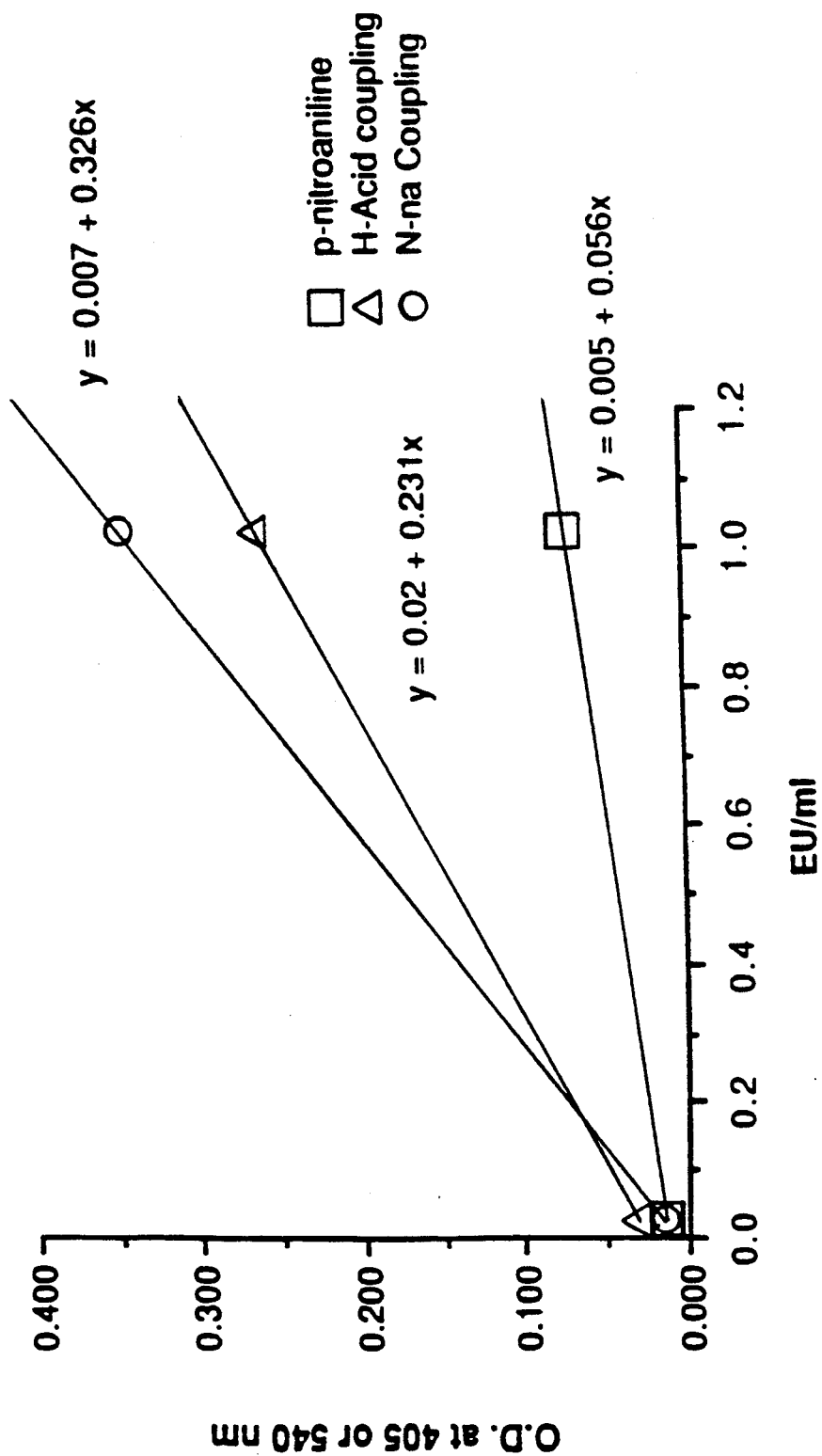
FIG. 2 shows relative values of optical densities for p-nitroaniline as such and its azo dyes with H-Acid and N-na. Reaction mixture volumes equal 5.0 cc.
Figure 3:
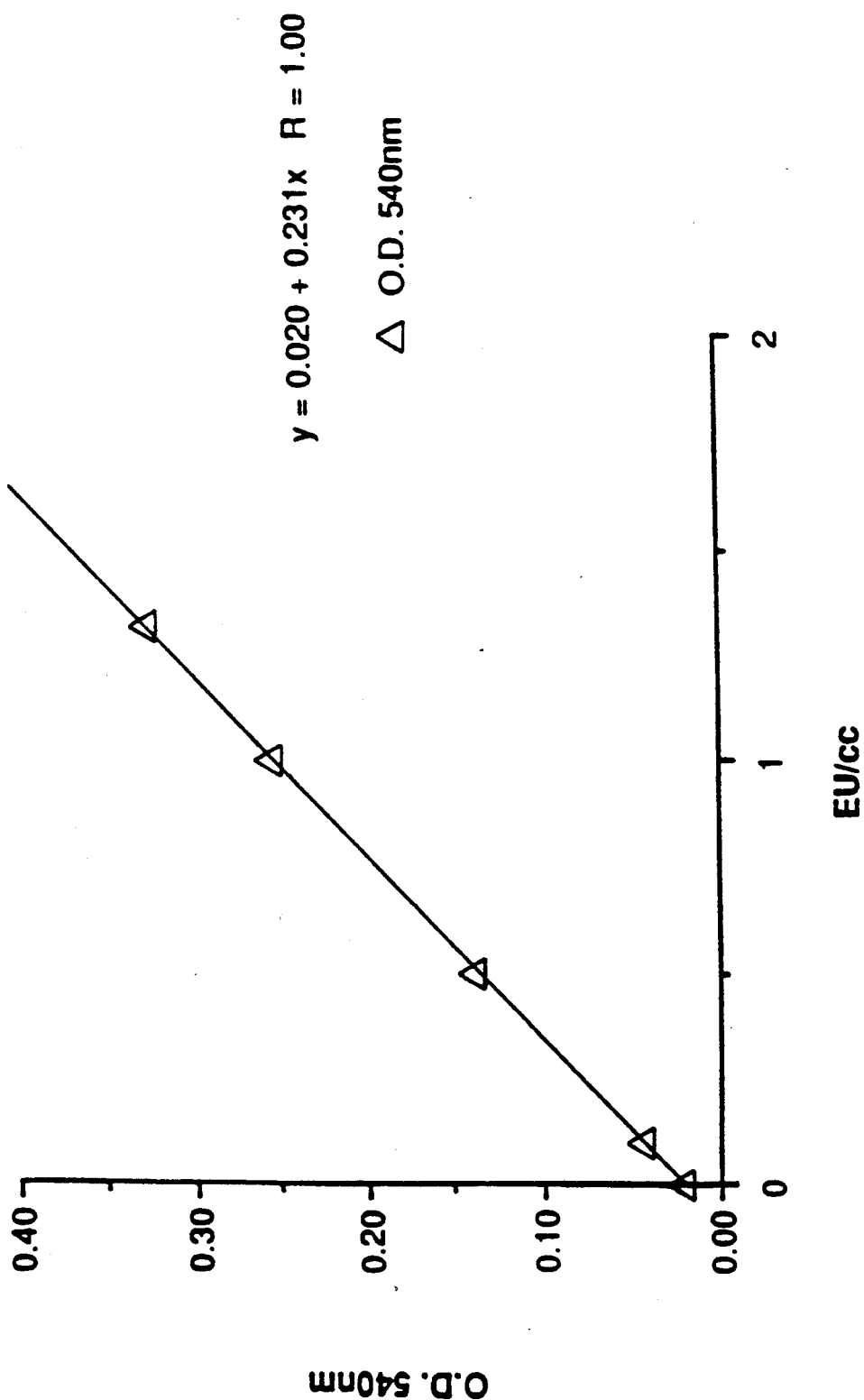
FIG. 3 shows endotoxin standard curve for p-nitroaniline coupled with H-Acid.
Figure 4:
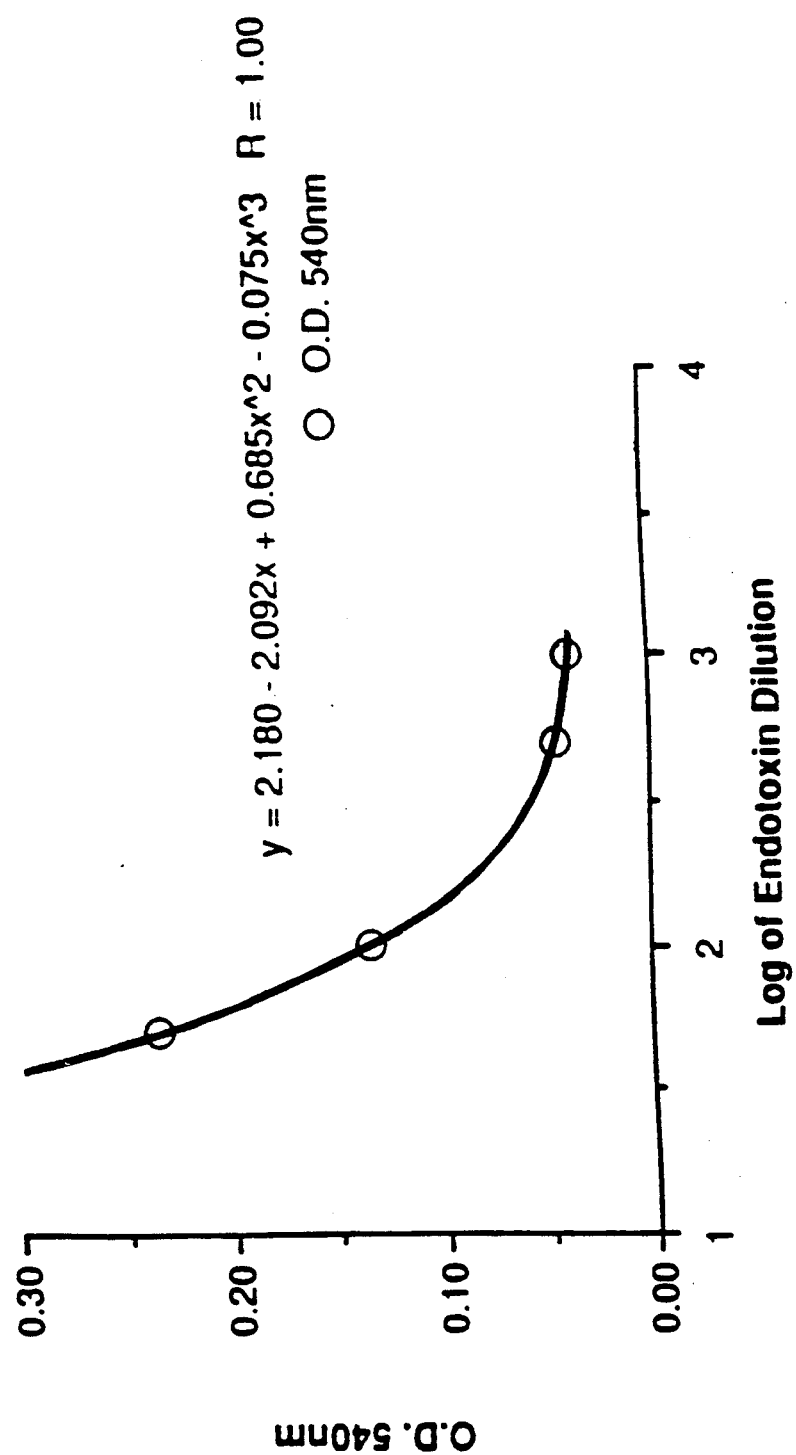
FIG. 4 shows optical densities of endotoxins eluted from a periodontal strip at various dilutions for p-nitroaniline coupled with H-Acid.
Figure 5:
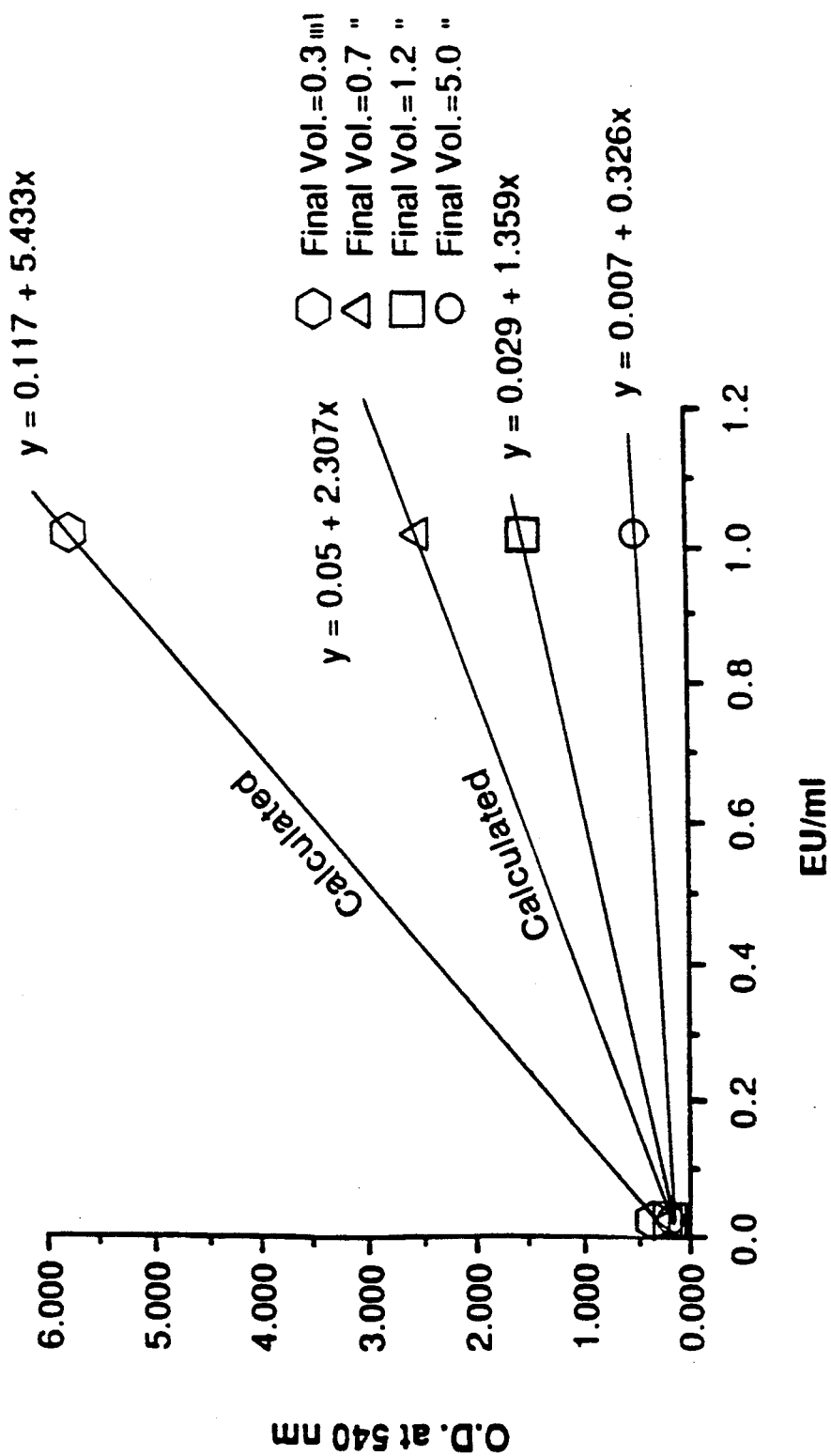
FIG. 5 shows optical densities of p-nitroaniline coupled with N-na at various concentrations of endotoxins in the reaction mixture.

The present invention concerns a method of quantitatively determining the amount of bacterial endotoxin present in a periodontal pocket of a subject. The method comprises:
 a) obtaining a sample from the periodontal pocket of the subject;
 b) contacting the sample with an amebocyte lysate under conditions so as to activate an enzyme capable of cleaving a bond between an arginyl group and a nitrogen-containing group;
 c) contacting the activated enzyme with a substrate comprising an arginyl group and a suitable nitrogen-containing group bound to the arginyl group so as to form an amine;
 d) treating the resulting amine to produce a detectable product; and
 e) quantitatively determining the amount of product formed and thereby the amount of bacterial endotoxins present in the periodontal pocket.

In the preferred embodiments, the method comprises treating the sample prior to contacting with the amebocyte lysate so as to inactivate enzymes present in the sample which would interfere with amebocyte lysate-endotoxin interaction, such as trypsin or trypsin-like enzymes.

The sample may also be diluted in order to reduce the effect of Gram-positive bacteria on the amebocyte lysate-endotoxin interaction. On the average the gram negative bacteria are approximately $1 \times 10^6$ times more active in the Limulus assay than any of the gram positive bacteria. Accordingly, the distinction between Gram-negative and Gram-positive bacteria can be readily ascertained and maximized by dilutions of plaque organisms in the sample. In this manner all Limulus provoking activity of Gram-positive bacteria can be minimized by the dilution effect and thus only gram negative bacteria will be capable of provoking a positive Limulus response. Since over 98% of the suspected periodontal pathogens are gram negative, the dilution of plaque organisms in the sample increases the effectiveness of the present method as a clinical tool for determining levels of gram negative bacteria in a pocket site and thereby the effectiveness of the method in diagnosing periodontal diseases.

The sample may be obtained by placing a small filter paper strip into a periodontal pocket of the subject and collecting the sample on the paper strip. In the preferred embodiments, the strip is then subjected to heating, e.g. hot air from a hair dryer set on high temperature for 1 minute, in order to inactivate endogenous enzymes present in the sample which may interfere with the amebocyte lysate-endotoxin reaction.

In carrying out the present method, the sample is mixed with a horseshoe crab amebocyte lysate, preferably Limulus amebocyte lysate. However, lysate from other forms of horseshoe crabs such as Tachypleus tridentatus, the Japanese horseshoe crab, can be used. The lysate can be prepared in accordance with conventional procedures. Procedures such as are disclosed in Journal of Clinical Investigation, Volume 51, July 1972, Bulletin of Johns Hopkins Hospital, Volume 115, pages 265–274 (1964) and Proceedings of the Society for Experimental Biochemical Medicine, Volume 137, pages 334–342, can be used to recover the lysate. Briefly, the conventional procedure usually involves withdrawing crab blood by sterile needle from the crab heart, placing the blood into a mixture which prevents aggregation of the blood cells and premature lysis of the cells, separating the amebocytes from the remainder of the blood by centrifugation, lysing the amebocytes by mechanical breaking, freeze-thawing or by osmotic lysis in pyrogen-free distilled water in a volume ratio of water to cells of about 3–6:1 or the like. The lysate thus obtained is centrifuged free of the broken cells and usually freeze dried, that is lyphophilized, to preserve it. When it is ready for use, the lysate powder is diluted with approximately 50 volumes of sterile pyrogen-free distilled water to bring it to a solids concentration per ml. of about 0.02 gm. In the present method, lysate is used which may either be one freshly prepared or one which has been preserved, usually in lyophilized powder form, and which has been reconstituted or which during the preparation of the reaction mixture is directly added as a powder to the liquid mixture. In any event, the lysate is present in a solids concentration in the reaction mixture of about 1.50 to about 2.50 gm/100 ml.

The substrate utilized in the present method contains a selected colorimetric indicator capable of being split off from the substrate by lysate enzyme produced by conversion of proenzyme by endotoxin in the sample.

For such purposes, any suitable substrate generally of the type described in, for example, U.S. Pat. No. 4,028,318 can be utilized. However, certain of such substrates have been found to be more advantageous than others. In this regard, substrates characterized by the general formula $R_1$-Ile-Glu-Gly-Arg-pNA are preferred.

The $R_1$ blocking group in the general formula above may be N-tert butoxycarbonyl, alkanoyl of 1 to 12 carbon atoms, cyclohexylcarbonyl, and N-benzoyl, acetyl and benzoyl substituted with one or more halogens, lower alkyl, e.g., methyl and ethyl, amino or phenyl groups, or may be H when the N-terminal L-amino acid of the peptide structure is replaced with a N-terminal D-amino acid. Suitable chromogenic or fluorogenic groups include nitrophenyl, methylnitrophenyl, dinitrophenyl, naphthyl, nitronaphthyl, methoxyhaphthhyl, indoxyl, methylindoxyl, (4-methyl-)umbelliferyl and resorfin.

The most preferred substrates comprise benzoyl (or acetyl)-isoleucine-glutamic acid-glycine-arginine-p-nitroanalide benzoylarginine-β-naphthylamide, benzoylarginine-p-nitroanilide. Further suitable substrates can easily be determined by minimal experimental testing. Such substrates may contain, for example, 2-naphthyl-amide as the color indicator or p-nitroanilide.

Also contemplated by the present invention are the acid addition salts of the above peptide-type compounds. Suitable acid salts include those from mineral acids such as hydrochloric, hydrobromic, hydrosulfuric and hydrophosphoric or from organic acids such as formic, cetic, oxalic, tartaric, methane sulfonic and benzene sulfonic.

In accordance with the present method, the desired test reaction is effected by mixing together the sample, the amebocyte lysate and the selected substrate in suitable relative concentrations. In carrying out the method the sample can, for example, be added to a reaction vessel such as a sterile test tube, can then be diluted with about five to ten volumes of pyrogen-free sterile water and powdered Limulus amebocyte lysate or other horseshoe crab amebocyte lysate in a suitable concentration can then be added to each such test tube. The temperature of each test tube is preferably kept within a suitable range, for example, 35°-40° C., most preferably about 37° C. This mixture is thoroughly mixed together and incubated for about 7-12 minutes, preferably about 10 minutes.

The substrate is then added to each test tube and the resulting mixture is then mixed together and incubated for about 2-4 minutes, preferably about 3 minutes, at the desired previously indicated temperature of about 37° C. for a total reaction time (initial incubation plus final incubation) of approximately 10-12 minutes, preferably about 11 minutes, whereupon acetic acid, for example, 1N, is added to each test tube in a volume sufficient to stop the reaction from continuing, usually 100 μl. The mixture is then left in each test tube and read on a colorimeter at 405 nm. The concentration of the endotoxin is calculated from a standard curve previously prepared from known dilutions of a standard endotoxin The method may also be performed by using a reagent sheet as described in the Experimental Detail section which follows.

Alternatively, the contacting of the sample with amebocyte lysate may be performed simultaneously with the contacting of the trypsin-like enzyme with the substrate. In one embodiment the sample is collected on a filter paper strip and contacted with a reagent sheet which contains the amebocyte lysate and the substrate. Preferably the sheet also contains a buffer, such as Tris. The sample on the filter paper strip may also be immersed in a solution containing the amebocyte lysate and the substrate or it may be immersed with the above described reagent sheet in a solution containing the buffer and/or pyrogen-free water.

The treating of the reaction mixture to produce a detectable product preferably consists of conversion of the amine to its a diazonium salt and reacting the diazonium salt with a suitable coupling agent to produce the detectable product. Suitable coupling agents are well known to those skilled in the art and include histidine, 8-amino-1-hydroxynapthalene-3,6-disulfonic acid, or N-(1-naphthyl)-ethylenediamine dihydrochloride or a salt thereof.

The invention also provides a method of diagnosing a periodontal disease which comprises quantitatively determining the amount of bacterial endotoxins present in a periodontal pocket of a subject by the method of the present invention and correlating the amount so determined with known periodontal disease-causing amounts of endotoxin. In the preferred embodiments the periodontal disease is gingivitis or advanced periodontitis.

Lastly, the invention provides a diagnostic kit for diagnosing periodontal diseases in a patient.

The invention is further illustrated in the Experimental Details section and the examples which follow. These sections are set forth to aid in an understanding of the invention but are not intended to, and should not be construed to, limit in any way the invention as set forth in the claims which follow thereafter.

EXPERIMENTAL DETAILS

Experiments performed in the laboratories of the inventors demonstrated a positive, strong correlation between stages of gingivitis and levels of endotoxin as measured by the Limulus lysate assay. In such experiments it was possible to quantitatively evaluate endotoxins obtained by placing a small filter paper strip into a single, minimally inflamed gingival pocket. Material eluted from the strip was quantitated by the Limulus lysate assay, and recorded as nanograms of endotoxin in a sample from the contents of one pocket site A correlation value of $r=0.95$ was observed between levels of gingivitis and Limulus lysate activity. Based on the results obtained in these initial experiments, work on a simple application of the Limulus lysate assay to make it conveniently applicable within the practical limits of the dental practitioner was performed. For this purpose a chromogenic substrate was utilized for developing a color following an endotoxin-Limulus lysate interaction.

The present invention involves the use of an extremely sensitive colorimetric or fluorometric assay for the determination of minute amounts (picograms, $10^{-12}$ grams) of specific biochemical constituents of Gram-negative bacteria in periodontal pockets. The method requires that the dental practitioner obtain a sample of the patient's periodontal pocket contents by a standardized method using small filter paper strips. A paper strip acts as a wick to collect bacteria and their free biochemical consituents contained in the pocket. The strip can be treated according to a "Dry-assay" or "Wet-assay" method. In the former case the strip is placed on a "Reagent sheet" containing buffering components and Limulus lysate ingredients. The site of the strip placed on the "Reagent sheet" is wetted with pyrogen-free water, and following an endotoxing-Limulus lysate interaction the color developed is compared with color intensities of a color chart. If the substrate is fluorogenic, the fluorescence developed is similarly evaluated by illuminating the reaction spot in a dark room. Color or fluorescence charts are made on the basis of amounts of endotoxin required under the standard conditions. Alternatively, in the "Wet-assay" method the sample strip and the "Reagent sheet" are immersed in 0.5 ml of pyrogen-free water for interaction and development of color or fluorescence measured with a colorimeter or fluorometer. Values obtained are examined with a standard curve of color or fluorescence versus amount of endotoxin. The reaction-developing color or fluorescence proceeds as the appropriate chromophore is freed by action of a trypsin-like enzyme generated from a zymogen form present in the Limulus lysate. Activation of the zymogen is the result of zymogen-endotoxin interaction. The intensity of color or fluorescence is a direct measure of any inflammatory substances present in the periodontal pocket, mostly bacterial endotoxins contributed by Gram-negative bacteria In this manner the dental practitioner can monitor Gram-negative bacteria and/or inflammatory agents contained in the periodontal pockets of a patient, and, therefore, have a quantitative criterion to follow up the success of the therapy applied.

EXAMPLES

TYPICAL LIMULUS AMEBOCYTE LYSATE (LAL) TEST using a chromogenic substrate according to the kit QCL-1000® by Whittaker M.A. Bioproducts.

Materials

Lyophilized LAL to be dissolved in 1.4 cc of pyrogen-free water.

*E. Coli* Endotoxin Standard (about 20 endotoxin units (EU)), to be dissolved in 1.0 cc of pyrogen-free water.

Acetyl-Ile-Glu-Gly-Arg-p-nitroanalide Substrate to be dissolved in 6 0 cc of pyrogen-free water (2.2 mM solution).

Tris Buffer, 0.05 M, pH 9.0, 0.2 ionic strength adjusted with NaCl, in the presence of $Ca^{++}$ and $Mg^{++}$ ions.

Pyrogen-Free Water.

Method

| Solution | Incubation Time and Temp. |
| --- | --- |
| 50 μl LAL | |
| 50 μl Buffer | 10 min, 37° |
| 50 μl Endotoxin Standard or unknown | |
| 50 μl Substrate | 3 min, 37° |
| 100 μl 25% Acetic acid | |
| Total Volume: 0.3 cc. | |
| Measure O.D. of p-Nitroaniline at 405 nm. | |

MODIFIED, CHROMOGENIC LIMULUS AMEBOCYTE LYSATE (LAL) TEST specifically developed for the evaluation of periodontal disease in dental office.

The main characteristics of the Modified Chromogenic LAL Test are:

1. An increase of the reaction mixture volume from 0.3 to 5.0 cc. Volume increase is necessary to permit the use of an inexpensive colorimeter instead of a special, expensive spectrophotometer used in a typical LAL test.

2. Possibility of visual comparison of strong red colorations instead of relatively weak yellow colorations due to p-nitroaniline. Red colorations are obtained by coupling p-nitroaniline with H-Acid (cherry-red) or with N-na (purplish red).

3. Minimal chance of error in a procedure performed by dental office personnel.

Materials

All materials are commercially available.

LAL, Endotoxin Standard, Chromogenic Substrate, Buffer and Pyrogen-Free Water, as provided in the QCL-1000 Kit by Whittaker M.A. Bioproducts.

For p-nitroaniline - H-Acid Coupling
1% Sodium Nitrite
3% Urea
6% Sodium Bicarbonate
0.75% H-Acid (8-amino-1-hydroxynaphthalene-3,6-disulfonic acid,Na salt.1.5 HOH)
0.05N HCl For p-nitroaniline - N-an Coupling:
1% Sodium Nitrite
3% Urea
0.75% N-na (N-(1-naphthyl)-ethylenediamine 0.2 HCl)
0.35N HCl H-Acid and N-na obtained from Aldrich Chemical Co.

Methods

The Modified LAL Test was developed in stages starting with an evaluation of the nature and conditions of the typical LAL test. In addition to the disadvantage of a 0.3 cc reaction mixture volume and the yellow coloration that is not an optimal criterion for visual comparisons in the typical LAL test, there are two undesirable conditions in this test:

1. The practice of a 10-min. incubation for the zymogen-enzyme conversion followed by the 3-min. enzyme-substrate interaction requires strict timing that may result in stress and errors on the part of those performing the tests especially when several samples are handled in one run. There is no reason for the substrate not to be present from the beginning, and acted upon as the enzyme is being generated. Therefore, it was decided to allow the total mixture of LAL, endotoxin, substrate and buffer to be held at 37 for 15 min.

The modification of the one-stage 15-min. total interaction is considerably safer with regard to timing errors than the typical LAL test characterized by a first stage 10-min. incubation followed by a second stage 3-min. enzymatic reaction. Furthermore, the 15-min. total interaction results in a higher concentration of p-nitroaniline generated.

2. There is no particular advantage in using 25% acetic acid in the typical LAL test. Thus, in the Modified LAL Test it was decided to use a solution of HCl with a dual purpose: first, to terminate the enzyme-substrate interaction, and second, to convert the generated p-nitroaniline into its diazonium salt to be coupled with the appropriate agent. The p-nitroaniline—H-Acid coupling was performed under alkaline conditions. Thus, 0.05N HCl was sufficient to terminate enzymatic activity and liberate the nitrous acid to interact with p-nitroaniline. For the p-nitroaniline—N-na coupling method 0.35N HCl was used to terminate enzymatic activity, form the diazonium salt of p-nitroaniline and provide the required acidity for coupling.

Experimental work began by maintaining the mixture of LAL, endotoxin, substrate and buffer at 37° for 15 min., and terminating enzymic activity with 0.5 cc of 0.05N (or 0.35N) HCl:

| | |
| --- | --- |
| 50 μl LAL | |
| 50 μl Buffer | |
| 50 μl Endotoxin Standard or unknown | |
| 50 μl Substrate | |
| 15 min., 37° | One-stage, 15 min. total interaction |
| 500 μl 0.05 N (or 0.35 N) HCl | |

The resulting final volume of 0.7 cc permitted p-nitroaniline O.D. measurements at 405 nm using an ordinary spectrophotometer and 1 cc cuvettes.

In subsequent work, 1.0 cc of acid was added giving a final volume of 1.2 cc. The 1.2 cc volume was appropriate for the formation of the p-nitroaniline diazonium salt followed by coupling to form an azo-dye. After coupling with H-Acid or N-na, either the reaction mixture was diluted to 5.0 cc and its O.D. was measured at 540 nm or sample and standard colorations were visually compared.

Modified LAL Test.p-nitroaniline coupled with H-Acid:
50 μl LAL
50 μl Buffer
50 μl Endotoxin Standard or Unknown or Control, in 50 μl Pyrogen-Free Water
50 μl Substrate
15 min., 37°
1.0 cc 0.05 N HCl
100 μl 1% Sodium Nitrite
100 μl 3% Urea
500 μl 6% Sodium Bicarbonate
100 μl 0.75% H-Acid

| -continued |  |
|---|---|
| Modified LAL Test. p-nitroaniline coupled with H-Acid: | |
| Water to 5.0 cc (3.1 cc) | O.D. measured at 540 nm |

Comments

Addition of sodium nitrite in the acid medium results in liberation of nitrous acid which in turn reacts with p-nitroaniline to form its diazonium salt.

Urea is added to destroy any excess nitrous acid, thus preventing a reaction of this acid with the amino group of the H-Acid.

Sodium bicarbonate provides the alkalinity for the H-Acid coupling.

The cherry-red color obtained was stable for weeks.

STRUCTURAL FORMULAE

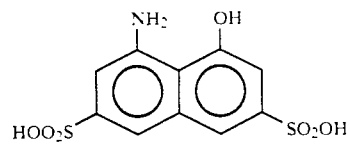

H-Acid (Free form)

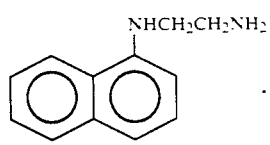

N-na (Free form)

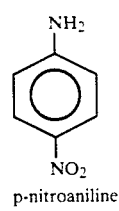

p-nitroaniline

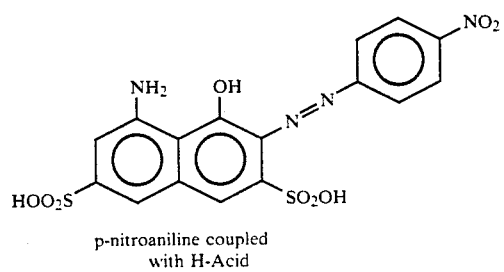

p-nitroaniline coupled with H-Acid

-continued
STRUCTURAL FORMULAE

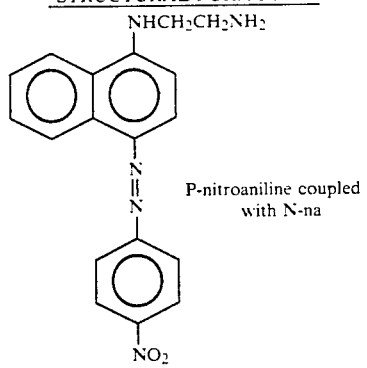

P-nitroaniline coupled with N-na

| Modified LAL Test. p-nitroaniline coupled with N-na: | |
|---|---|
| 50 μl LAL | |
| 50 μl Buffer | |
| 50 μl Endotoxin Standard or Unknown Control. with 50 μl Pyrogen Free Water | |
| 50 μl Substrate | |
| 15 min., 37° | |
| 1.0 cc 0.35 N HCl | |
| 100 μl 1% Sodium Nitrite | |
| 100 μl 3% Urea | |
| 100 μl 0.75% H-na | |
| Water to 5.0 cc (3.5 cc) | O.D. measured at 540 nm |

Comments

Under the conditions of acidity and 1.4 cc volume prior to addition of N-na, introduction of this coupler results in instantaneous formation of a purplish color. The color is practically unchanged for 24 hours, but fades in about two weeks to an extent visually observed in a comparison of fresh and old reaction mixtures.

The O.D. of N-na coupled reaction mixtures is about 1.4 times higher than the O.D. associated with H-Acid coupling and about 6 times higher than the O.D. of the p-nitroaniline not subjected to coupling.

Modified LAL Test for endotoxins obtained from the fluid of a periodontal pocket:

Fluid of periodontal pockets was sampled by inserting the professionally employed paper strips for 30 sec. 1.0 cc of buffer was added to a strip and the mixture was gently warmed and vortexed for one min. This master solution of endotoxins was diluted with pyrogen-free water 50, 100, 500 and 1000 times. The Modified LAL Test was performed only with diluted solutions because master solutions of endotoxins exhibited a concentration that was over-saturating the LAL material. It is noted that a certain amount of LAL material contains a certain amount of zymogen that is converted to an enzyme in proportion to the amount of endotoxin. Endotoxin supplied in excess of the requirement for the total zymogen present is useless and no more enzyme can be generated. Accordingly, excess endotoxin is manifested as a plateau effect for the p-nitroaniline liberated

EXAMPLE

Measuring the Endotoxins of a Periodontal Pocket:

A strip was inserted for 30 sec. in a 6-mm periodontal pocket of a patient with advanced periodontitis. The strip was eluted in 1.0 cc of buffer to form a master solution of endotoxins. A Modified LAL Test with H-Acid coupling was performed using 100 μl of the 50 times diluted master solution of endotoxins. An O.D. of 0.234 was measured at 540 nm.

According to the Standard Endotoxin Curve (linear function) prepared under identical conditions, an O.D. of 0.234 at 540 nm corresponds to an endotoxin concentration of 0.93 EU/cc (Endotoxin Units/cc).

Therefore, the 50 times diluted solution of endotoxins had an endotoxin concentration of 0.93 EU/cc. Thus, the endotoxin concentration in 1.0 cc of strip eluate (master solution) exhibited an endotoxin content of 46.5 EU/cc (0.93×50).

The Endotoxin Standard Curve:

As mentioned in the Materials section for the typical LAL test, Standard *E. Coli* Endotoxin is supplied with a specification of X Endotoxin Units/vial (EU/vial). Addition of 1.0 cc of Pyrogen-Free Water yields a Standard Endotoxin Solution of X EU/cc. One Endotoxin Unit represents 0.2 nanograms of LPS (lipopolysaccharide).

It is convenient to dilute an original Standard Endotoxin solution of X EU/cc X times in order to obtain a Standard Endotoxin solution of 1.0 EU/cc, an aliquot of which can be further diluted (e.g., 2, 4, 5 and 10 times).

The 1.0 EU/cc solution and its further dilutions are used to perform a LAL test and plot O.D. measured versus EU/cc of endotoxin solution employed.

General Considerations concerning the Modified Chromogenic LAL Test:

The spectrophotometric determinations of aniline and many of its derivatives based on procedures of diazotization-coupling were reported by George Norwitz and Peter Keliher Anal. Chem. 53, 56–60 (1981); Anal. Chem. 53, 1238–1240 (1981); Anal. Chem. 54, 807–809 (1982); Anal. Chem. 55, 1226–1229 (1983)). Norwitz and Kellher selected H-Acid and N-na for diazotization-coupling with aniline and its derivatives and investigated the conditions of the reactions for the production of azo dyes that are reliable and useful in spectrophotometry.

However, in this work certain of Norwitz's and Kellher's conditions were modified for practical purposes. For instance, the coupling agents were added to a considerably smaller volume of solutions containing the diazonium salt of p-nitroaniline to achieve higher concentrations and faster reactivity. Also, urea, a substance less costly than ammonium sulfamate, was employed to destroy excess nitrous acid.

H-Acid and N-na, like all aromatic hydrocarbons and their derivatives, are substances that must be handled with care. For reasons of safety and also because H-Acid (not recrystallized material) solutions darken upon standing even without exposure to light, it was necessary to seek an alternative to the use of coupling agent solutions Strips cut from thick glass-fiber filtration disks (Whatman) were wetted with coupling agent solutions and allowed to dry. Such dry coupling reagent-strips were successfully used for the addition of the coupling agents. There was an immediate development of red color of the same optical density as in the case of addition of fresh coupling reagent solution.

The Modified LAL Tests were also performed as "spot tests" on thick glass-fiber filtration disks However, the above-described methods are more appropriate for a visual comparison of colorations in solutions held in the path of light.

Optical densities of low value observed in control experiments (Pyrogen-Free Water added instead of Endotoxin Solution) are due to the spontaneous hydrolysis of the substrate exposed to pH 9, at 37° C. For this reason the substrate solution is prepared with pyrogen-free water, and can be kept refrigerated for about six months without a significant release of p-nitroaniline. The substrate is exposed to the buffer only during the performance of a LAL test.

To date the Limulus activity of the following 9 oral isolates have been analysed (1)—Gram-positive bacteria including—*S. mutans, S. sanguis, A. israelii, A. viscosus, A. neaslundi;* (2)—Gram-negative bacteria including—*C. gingivalis, C. ochracea, A. actinomycetemcomitans,* and *V. alcalescens.*

On the average the Gram-negative bacteria are approximately $1 \times 10^6$ times more active in the Limulus Assay than any of the Gram-positive bacteria tested using the clot and tube dilution assay. Negligible differences were found when whole cell suspensions were compared to sonic extracts derived from analogous whole cell suspensions. Thus it can be assumed that either whole cells or cell fragments derived from the same cell source can provoke Limulus activity with equal facility These results suggest that distinctions between Gram-negative and Gram-positive bacteria can be readily ascertained and maximized by dilutions of plaque organisms. In this manner all Limulus-provoking activity of Gram-positive bacteria can be obliterated by the dilution effect and thus only Gram-negative bacteria will be capable of provoking a positive Limulus response. Since over 98% of the suspected periodontal pathogens are Gram-negative this could be a valuable clinical tool for determining levels of Gram-negative bacteria in a pocket site.

A collection procedure that can be used at chairside by dentists in an effort to determine levels of endotoxin in specific pocket areas has been developed (see Example below).

PROTOCOL FOR SAMPLE COLLECTION (1)—Isolate area with cotton rolls
(2)—Wipe area dry with cotton pledget
(3)—Place one #3 sterile absorbent endodontic paper point into pocket of concern for ten seconds
(4)—Holding point with tweezers dry point with air from hair dryer set on high temperature for one minute
(5)—Place paper point in sterile tube, label tube and place in freezer
(6)—Try to collect from 2 diseased sites and one "normal" site per patient
(7)—Perform LAL test or modified LAL test on paper point and determine endotoxin concentration by comparison with color charts.

What is claimed:

1. A method of quantitatively determining the amount of bacterial endotoxins present in a periodontal pocket of a subject which comprises:
   (a) collecting a sample from the periodontal pocket of the subject on a filter paper strip by placing the strip momentarily in the periodontal pocket;
   (b) dry heating the strip containing the sample so as to inactivate endogenous enzymes which would interfere with Limulus amebocyte lysate-endotoxin interaction;
   (c) contacting the dry heated strip with Limulus amebocyte lysate and a substrate comprising an arginyl group and a naphthylamide or p-nitroanilide group bound to the arginyl group so as to form an aromatic amine;
(d) treating the aromatic amine to form a diazonium salt;
(e) reacting the diazonium salt with a suitable coupling agent to produce a visually colored product; and
(f) quantitatively determining the amount of colored product produced and thereby the amount of bacterial endotoxins present in the periodontal pocket by comparing the color intensity of the colored product to standards of known endotoxin concentrations.

2. A method of diagnosing a periodontal disease which comprises quantitatively determining the amount of endotoxin present in the periodontal pockets of a subject by the method of claim 1 and correlating the amount so determined with known periodontal disease-causing amounts of endotoxin.

3. A method of claim 2, wherein the periodontal disease is gingivitis or advanced periodontitis.

4. A method of quantitatively determining the amount of bacterial endotoxins in a periodontal pocket of a subject which comprises:
(a) collecting a sample from the periodontal pocket of the subject on a filter paper strip by placing the strip momentarily in the periodontal pocket;
(b) dry heating the strip containing the sample so as to inactivate endogenous enzymes which would interfere with Limulus amebocyte lysate-endotoxin interaction;
(c) contacting the dry heated strip containing the sample with a Limulus amebocyte lysate under conditions so as to activate a proenzyme contained in the Limulus amebocyte lysate, the resulting enzyme being capable of cleaving a bond between an arginyl group and a nitrogen-containing group, such that the sample contains the enzyme;
(d) contacting the enzyme contained in the resulting sample with a substrate selected from the group consisting of benzoylarginine-β-naphthylamide, benzoylarginine-p-nitroanilide, or acetyl-Ileu-Glu-Gly-Arg-(p-nitroanilide) so as to form an amine;
(e) treating the resulting amine to produce a visually detectable product; and
(f) quantitatively determining the amount of the product formed and thereby the amount of bacterial endotoxins present in the periodontal pocket.

5. A method of claim 4, wherein the contacting of the dry heated strip containing the sample with the Limulus amebocyte lysate is performed in the presence of a buffer.

6. A method of claim 4, wherein the dry heated strip containing the sample is contacted simultaneously with Limulus amebocyte lysate and the substrate.

7. A method of claim 6, wherein the contacting is effected by contacting the strip with a reagent sheet containing the Limulus amebocyte lysate and the substrate.

8. A method of claim 6, wherein the contacting is effected by immersing the strip in a solution comprising the Limulus amebocyte lysate and the substrate.

9. A method of claim 4, wherein the amine formed is naphthylamine or p-nitroaniline.

10. A method of claim 4, wherein the treating of the amine comprises diazotization of the amine to produce a diazonium salt and reacting the diazonium salt with a suitable coupling agent to produce a visually detectable product.

11. A method of claim 10, wherein the coupling agent is histidine, 8-amino-1-hydroxynapthalene-3,6-disulfonic acid, or N-(1-naphthyl)-ethylenediamine dihydrochloride or a salt thereof.

12. A method of claim 10, wherein the detectable product is a colored product.

13. A method of claim 4, wherein quantitatively determining the product formed is effected by comparing the detectable product with standards of known endotoxin concentrations.

14. A method of claim 4, wherein quantitatively determining the colored product is effected by comparing the colored product to standard curves of color versus endotoxin concentrations.

15. A method of claim 4, wherein quantitatively determining the colored product is effected by comparing the optical density of the colored product to optical densities of solutions of known endotoxin concentration.

* * * * *